(12) United States Patent
Park et al.

(10) Patent No.: US 8,563,327 B2
(45) Date of Patent: Oct. 22, 2013

(54) DIAGNOSTIC MARKER FOR TYPE 1 DIABETES MELLITUS

(75) Inventors: Sang Gyu Park, Seoul (KR); Kyong Soo Park, Seoul (KR); Sunghoon Kim, Seoul (KR)

(73) Assignees: Seoul National University Hospital, Seoul (KR); SNU R&DB Foundation, Seoul (KR)

( * ) Notice: Subject to any disclaimer, the term of this patent is extended or adjusted under 35 U.S.C. 154(b) by 0 days.

(21) Appl. No.: 13/198,990

(22) Filed: Aug. 5, 2011

(65) Prior Publication Data

US 2012/0015383 A1   Jan. 19, 2012

Related U.S. Application Data

(63) Continuation of application No. PCT/KR2010/000710, filed on Feb. 5, 2010.

(30) Foreign Application Priority Data

Feb. 5, 2009   (KR) .................. 10-2009-0009231

(51) Int. Cl.
| | |
|---|---|
| G01N 33/564 | (2006.01) |
| G01N 33/536 | (2006.01) |
| G01N 33/543 | (2006.01) |
| G01N 33/573 | (2006.01) |
| G01N 33/66 | (2006.01) |
| C07K 16/40 | (2006.01) |

(52) U.S. Cl.
USPC .......... 436/506; 435/6.19; 435/7.1; 435/7.21; 435/7.4; 435/15; 435/973; 435/975; 436/518; 436/536; 436/543; 436/15; 436/67; 436/811; 530/388.26; 530/389.1; 530/395; 530/403; 530/845

(58) Field of Classification Search
USPC .......... 435/6.19, 7.1, 7.21, 7.4, 15, 973, 975; 436/506, 518, 536, 543, 15, 811, 67; 530/388.26, 389.1, 395, 403, 845
See application file for complete search history.

(56) References Cited

U.S. PATENT DOCUMENTS

| | | | | |
|---|---|---|---|---|
| 2005/0118151 | A1* | 6/2005 | Larsen et al. | 424/93.21 |
| 2006/0073134 | A1* | 4/2006 | Larsen et al. | 424/130.1 |
| 2009/0075832 | A1* | 3/2009 | Neuman et al. | 506/9 |

OTHER PUBLICATIONS

Baekkeskov et al., 1982. Autoantibodies in newly diagnosed diabetic children immunoprecipitate human pancreatic islet cell proteins. Nature 298: 167-169.*
Christie et al., 1993. Detection of pancreatic islet 64,000 Mr autoantigens in insulin-dependent diabetes distiinct from glutamate decarboxylase. J. Clinical Invest. 92: 240-248.*
Hirakata et al., 1999. Anti-KS: identification of autoantibodies to asparaginyl-transfer RNA synthetase associated with interstitial lund disease. J. Immunol. 162: 2315-2320.*
Park et al., 2010. Autoantibodies against aminoacyl-tRNA synthetase: novel diagnostic marker for type 1 diabetes mellitus. Biomarkers 15: 358-366.*
Hueber et al., 2002. Autoantibody profiling for the study and treatment of autoimmune disease. Arthritis Res. 4: 290-295.*
Koenig et al., 2007. Heterogeneity of autoantibodies in 100 patients with autoimmune myositis: insights into clinical features and outcomes. Arthritis Res. Ther. 9: R78, pp. 1-13.*
Kron et al., 2005. Do tissue levels of autoantigenic aminoacyl-tRNA synthetase predict clinical disease? Medical Hypotheses 65: 1124-1127.*
Park et al., 2008. Aminoacyl tRNA synthetases and their connections to disease. PNAS 105: 11043-11049.*
Robinson et al., 2002. Autoantigen microarrays for multiplex characterization of autoantibody responses. Nature Medicine 8: 295-301.*
Verge et al., 1998. Combined use of autoantibodies (IA-2 autoantibody, GAD autoantibody, Insulin autoantibody, Cytoplasmic Islet Cell Antibodies) in type 1 diabetes. Diabetes 47: 1857-1866.*

* cited by examiner

*Primary Examiner* — Mark Shibuya
*Assistant Examiner* — James L Grun
(74) *Attorney, Agent, or Firm* — Edwards Wildman Palmer LLP

(57) ABSTRACT

The present invention provides, as a novel diagnosis marker for type 1 diabetes mellitus, a type 1 diabetes mellitus diagnostic composition comprising alanyl-tRNA synthetase, glycyl-tRNA synthetase, asparaginyl-tRNA synthetase, or tryptophanyl-tRNA synthetase, a diagnostic kit comprising the same, and a diagnostic method using the same. The composition, the kit, and the method, according to the present invention, may be used for early diagnosis and confirmed diagnosis of type 1 diabetes mellitus because type 1 diabetes mellitus can be easily diagnosed from a patient sample.

4 Claims, 2 Drawing Sheets
(2 of 2 Drawing Sheet(s) Filed in Color)

SEQUENCE LISTING

<160> NUMBER OF SEQ ID NOS: 8

<210> SEQ ID NO 1
<211> LENGTH: 968
<212> TYPE: PRT
<213> ORGANISM: Homo sapiens

<400> SEQUENCE: 1

```
Met Asp Ser Thr Leu Thr Ala Ser Glu Ile Arg Gln Arg Phe Ile Asp
  1               5                  10                  15

Phe Phe Lys Arg Asn Glu His Thr Tyr Val His Ser Ser Ala Thr Ile
             20                  25                  30

Pro Leu Asp Asp Pro Thr Leu Leu Phe Ala Asn Ala Gly Met Asn Gln
             35                  40                  45

Phe Lys Pro Ile Phe Leu Asn Thr Ile Asp Pro Ser His Pro Met Ala
 50                  55                  60

Lys Leu Ser Arg Ala Ala Asn Thr Gln Lys Cys Ile Arg Ala Gly Gly
 65                  70                  75                  80

Lys Gln Asn Asp Leu Asp Asp Val Gly Lys Asp Val Tyr His His Thr
                 85                  90                  95

Phe Phe Glu Met Leu Gly Ser Trp Ser Phe Gly Asp Tyr Phe Lys Glu
            100                 105                 110

Leu Ala Cys Lys Met Ala Leu Glu Leu Leu Thr Gln Glu Phe Gly Ile
            115                 120                 125

Pro Ile Glu Arg Leu Tyr Val Thr Tyr Phe Gly Gly Asp Glu Ala Ala
130                 135                 140

Gly Leu Glu Ala Asp Leu Glu Cys Lys Gln Ile Trp Gln Asn Leu Gly
145                 150                 155                 160

Leu Asp Asp Thr Lys Ile Leu Pro Gly Asn Met Lys Asp Asn Phe Trp
                165                 170                 175

Glu Met Gly Asp Thr Gly Pro Cys Gly Pro Cys Ser Glu Ile His Tyr
            180                 185                 190

Asp Arg Ile Gly Gly Arg Asp Ala Ala His Leu Val Asn Gln Asp Asp
            195                 200                 205

Pro Asn Val Leu Glu Ile Trp Asn Leu Val Phe Ile Gln Tyr Asn Arg
210                 215                 220

Glu Ala Asp Gly Ile Leu Lys Pro Leu Pro Lys Lys Ser Ile Asp Thr
225                 230                 235                 240

Gly Met Gly Leu Glu Arg Leu Val Ser Val Leu Gln Asn Lys Met Ser
                245                 250                 255

Asn Tyr Asp Thr Asp Leu Phe Val Pro Tyr Phe Glu Ala Ile Gln Lys
            260                 265                 270

Gly Thr Gly Ala Arg Pro Tyr Thr Gly Lys Val Gly Ala Glu Asp Ala
            275                 280                 285

Asp Gly Ile Asp Met Ala Tyr Arg Val Leu Ala Asp His Ala Arg Thr
290                 295                 300

Ile Thr Val Ala Leu Ala Asp Gly Gly Arg Pro Asp Asn Thr Gly Arg
305                 310                 315                 320

Gly Tyr Val Leu Arg Arg Ile Leu Arg Arg Ala Val Arg Tyr Ala His
                325                 330                 335

Glu Lys Leu Asn Ala Ser Arg Gly Phe Phe Ala Thr Leu Val Asp Val
            340                 345                 350

Val Val Gln Ser Leu Gly Asp Ala Phe Pro Glu Leu Lys Lys Asp Pro
            355                 360                 365
```

```
Asp Met Val Lys Asp Ile Ile Asn Glu Glu Val Gln Phe Leu Lys
    370                 375                 380

Thr Leu Ser Arg Gly Arg Ile Leu Asp Arg Lys Ile Gln Ser Leu
385                 390                 395                 400

Gly Asp Ser Lys Thr Ile Pro Gly Asp Thr Ala Trp Leu Leu Tyr Asp
                    405                 410                 415

Thr Tyr Gly Phe Pro Val Asp Leu Thr Gly Leu Ile Ala Glu Glu Lys
                420                 425                 430

Gly Leu Val Val Asp Met Asp Gly Phe Glu Glu Arg Lys Leu Ala
                435                 440                 445

Gln Leu Lys Ser Gln Gly Lys Gly Ala Gly Gly Glu Asp Leu Ile Met
    450                 455                 460

Leu Asp Ile Tyr Ala Ile Glu Glu Leu Arg Ala Arg Gly Leu Glu Val
465                 470                 475                 480

Thr Asp Asp Ser Pro Lys Tyr Asn Tyr His Leu Asp Ser Ser Gly Ser
                    485                 490                 495

Tyr Val Phe Glu Asn Thr Val Ala Thr Val Met Ala Leu Arg Arg Glu
                500                 505                 510

Lys Met Phe Val Glu Glu Val Ser Thr Gly Gln Glu Cys Gly Val Val
                515                 520                 525

Leu Asp Lys Thr Cys Phe Tyr Ala Glu Gln Gly Gly Gln Ile Tyr Asp
    530                 535                 540

Glu Gly Tyr Leu Val Lys Val Asp Asp Ser Ser Glu Asp Lys Thr Glu
545                 550                 555                 560

Phe Thr Val Lys Asn Ala Gln Val Arg Gly Gly Tyr Val Leu His Ile
                    565                 570                 575

Gly Thr Ile Tyr Gly Asp Leu Lys Val Gly Asp Gln Val Trp Leu Phe
                580                 585                 590

Ile Asp Glu Pro Arg Arg Pro Ile Met Ser Asn His Thr Ala Thr
                595                 600                 605

His Ile Leu Asn Phe Ala Leu Arg Ser Val Leu Gly Glu Ala Asp Gln
    610                 615                 620

Lys Gly Ser Leu Val Ala Pro Asp Arg Leu Arg Phe Asp Phe Thr Ala
625                 630                 635                 640

Lys Gly Ala Met Ser Thr Gln Gln Ile Lys Lys Ala Glu Glu Ile Ala
                    645                 650                 655

Asn Glu Met Ile Glu Ala Ala Lys Ala Val Tyr Thr Gln Asp Cys Pro
                660                 665                 670

Leu Ala Ala Ala Lys Ala Ile Gln Gly Leu Arg Ala Val Phe Asp Glu
                675                 680                 685

Thr Tyr Pro Asp Pro Val Arg Val Val Ser Ile Gly Val Pro Val Ser
                690                 695                 700

Glu Leu Leu Asp Asp Pro Ser Gly Pro Ala Gly Ser Leu Thr Ser Val
705                 710                 715                 720

Glu Phe Cys Gly Gly Thr His Leu Arg Asn Ser Ser His Ala Gly Ala
                    725                 730                 735

Phe Val Ile Val Thr Glu Glu Ala Ile Ala Lys Gly Ile Arg Arg Ile
                740                 745                 750

Val Ala Val Thr Gly Ala Glu Ala Gln Lys Ala Leu Arg Lys Ala Glu
                755                 760                 765

Ser Leu Lys Lys Cys Leu Ser Val Met Glu Ala Lys Val Lys Ala Gln
    770                 775                 780

Thr Ala Pro Asn Lys Asp Val Gln Arg Glu Ile Ala Asp Leu Gly Glu
```

```
                785                 790                 795                 800
Ala Leu Ala Thr Ala Val Ile Pro Gln Trp Gln Lys Asp Glu Leu Arg
                    805                 810                 815

Glu Thr Leu Lys Ser Leu Lys Lys Val Met Asp Asp Leu Asp Arg Ala
                820                 825                 830

Ser Lys Ala Asp Val Gln Lys Arg Val Leu Glu Lys Thr Lys Gln Phe
                835                 840                 845

Ile Asp Ser Asn Pro Asn Gln Pro Leu Val Ile Leu Glu Met Glu Ser
            850                 855                 860

Gly Ala Ser Ala Lys Ala Leu Asn Glu Ala Leu Lys Leu Phe Lys Met
865                 870                 875                 880

His Ser Pro Gln Thr Ser Ala Met Leu Phe Thr Val Asp Asn Glu Ala
                    885                 890                 895

Gly Lys Ile Thr Cys Leu Cys Gln Val Pro Gln Asn Ala Ala Asn Arg
                900                 905                 910

Gly Leu Lys Ala Ser Glu Trp Val Gln Gln Val Ser Gly Leu Met Asp
                915                 920                 925

Gly Lys Gly Gly Lys Asp Val Ser Ala Gln Ala Thr Gly Lys Asn
            930                 935                 940

Val Gly Cys Leu Gln Glu Ala Leu Gln Leu Ala Thr Ser Phe Ala Gln
945                 950                 955                 960

Leu Arg Leu Gly Asp Val Lys Asn
                    965

<210> SEQ ID NO 2
<211> LENGTH: 685
<212> TYPE: PRT
<213> ORGANISM: Homo sapiens

<400> SEQUENCE: 2

Met Asp Gly Ala Gly Ala Glu Glu Val Leu Ala Pro Leu Arg Leu Ala
  1               5                  10                  15

Val Arg Gln Gln Gly Asp Leu Val Arg Lys Leu Lys Glu Asp Lys Ala
                20                  25                  30

Pro Gln Val Asp Val Asp Lys Ala Val Ala Glu Leu Lys Ala Arg Lys
            35                  40                  45

Arg Val Leu Glu Ala Lys Glu Leu Ala Leu Gln Pro Lys Asp Asp Ile
        50                  55                  60

Val Asp Arg Ala Lys Met Glu Asp Thr Leu Lys Arg Arg Phe Phe Tyr
 65                  70                  75                  80

Asp Gln Ala Phe Ala Ile Tyr Gly Gly Val Ser Gly Leu Tyr Asp Phe
                    85                  90                  95

Gly Pro Val Gly Cys Ala Leu Lys Asn Asn Ile Ile Gln Thr Trp Arg
                100                 105                 110

Gln His Phe Ile Gln Glu Glu Gln Ile Leu Glu Ile Asp Cys Thr Met
            115                 120                 125

Leu Thr Pro Glu Pro Val Leu Lys Thr Ser Gly His Val Asp Lys Phe
130                 135                 140

Ala Asp Phe Met Val Lys Asp Val Lys Asn Gly Glu Cys Phe Arg Ala
145                 150                 155                 160

Asp His Leu Leu Lys Ala His Leu Gln Lys Leu Met Ser Asp Lys Lys
                    165                 170                 175

Cys Ser Val Glu Lys Lys Ser Glu Met Glu Ser Val Leu Ala Gln Leu
                180                 185                 190

Asp Asn Tyr Gly Gln Gln Glu Leu Ala Asp Leu Phe Val Asn Tyr Asn
```

-continued

```
              195                 200                 205
Val Lys Ser Pro Ile Thr Gly Asn Asp Leu Ser Pro Pro Val Ser Phe
210                 215                 220

Asn Leu Met Phe Lys Thr Phe Ile Gly Pro Gly Gly Asn Met Pro Gly
225                 230                 235                 240

Tyr Leu Arg Pro Glu Thr Ala Gln Gly Ile Phe Leu Asn Phe Lys Arg
                245                 250                 255

Leu Leu Glu Phe Asn Gln Gly Lys Leu Pro Phe Ala Ala Ala Gln Ile
                260                 265                 270

Gly Asn Ser Phe Arg Asn Glu Ile Ser Pro Arg Ser Gly Leu Ile Arg
                275                 280                 285

Val Arg Glu Phe Thr Met Ala Glu Ile Glu His Phe Val Asp Pro Ser
290                 295                 300

Glu Lys Asp His Pro Lys Phe Gln Asn Val Ala Asp Leu His Leu Tyr
305                 310                 315                 320

Leu Tyr Ser Ala Lys Ala Gln Val Ser Gly Gln Ser Ala Arg Lys Met
                325                 330                 335

Arg Leu Gly Asp Ala Val Glu Gln Gly Val Ile Asn Asn Thr Val Leu
                340                 345                 350

Gly Tyr Phe Ile Gly Arg Ile Tyr Leu Tyr Leu Thr Lys Val Gly Ile
                355                 360                 365

Ser Pro Asp Lys Leu Arg Phe Arg Gln His Met Glu Asn Glu Met Ala
370                 375                 380

His Tyr Ala Cys Asp Cys Trp Asp Ala Glu Ser Lys Thr Ser Tyr Gly
385                 390                 395                 400

Trp Ile Glu Ile Val Gly Cys Ala Asp Arg Ser Cys Tyr Asp Leu Ser
                405                 410                 415

Cys His Ala Arg Ala Thr Lys Val Pro Leu Val Ala Glu Lys Pro Leu
                420                 425                 430

Lys Glu Pro Lys Thr Val Asn Val Gln Phe Glu Pro Ser Lys Gly
                435                 440                 445

Ala Ile Gly Lys Ala Tyr Lys Lys Asp Ala Lys Leu Val Met Glu Tyr
450                 455                 460

Leu Ala Ile Cys Asp Glu Cys Tyr Ile Thr Glu Ile Glu Met Leu Leu
465                 470                 475                 480

Asn Glu Lys Gly Glu Phe Thr Ile Glu Thr Glu Gly Lys Thr Phe Gln
                485                 490                 495

Leu Thr Lys Asp Met Ile Asn Val Lys Arg Phe Gln Lys Thr Leu Tyr
                500                 505                 510

Val Glu Glu Val Val Pro Asn Val Ile Glu Pro Ser Phe Gly Leu Gly
                515                 520                 525

Arg Ile Met Tyr Thr Val Phe Glu His Thr Phe His Val Arg Glu Gly
                530                 535                 540

Asp Glu Gln Arg Thr Phe Phe Ser Phe Pro Ala Val Val Ala Pro Phe
545                 550                 555                 560

Lys Cys Ser Val Leu Pro Leu Ser Gln Asn Gln Glu Phe Met Pro Phe
                565                 570                 575

Val Lys Glu Leu Ser Glu Ala Leu Thr Arg His Gly Val Ser His Lys
                580                 585                 590

Val Asp Asp Ser Ser Gly Ser Ile Gly Arg Arg Tyr Ala Arg Thr Asp
                595                 600                 605

Glu Ile Gly Val Ala Phe Gly Val Thr Ile Asp Phe Asp Thr Val Asn
610                 615                 620
```

-continued

```
Lys Thr Pro His Thr Ala Thr Leu Arg Asp Arg Asp Ser Met Arg Gln
625                 630                 635                 640

Ile Arg Ala Glu Ile Ser Glu Leu Pro Ser Ile Val Gln Asp Leu Ala
            645                 650                 655

Asn Gly Asn Ile Thr Trp Ala Asp Val Glu Ala Arg Tyr Pro Leu Phe
        660                 665                 670

Glu Gly Gln Glu Thr Gly Lys Lys Glu Thr Ile Glu Glu
    675                 680                 685

<210> SEQ ID NO 3
<211> LENGTH: 548
<212> TYPE: PRT
<213> ORGANISM: Homo sapiens

<400> SEQUENCE: 3

Met Val Leu Ala Glu Leu Tyr Val Ser Asp Arg Glu Gly Ser Asp Ala
 1               5                  10                  15

Thr Gly Asp Gly Thr Lys Glu Lys Pro Phe Lys Thr Gly Leu Lys Ala
            20                  25                  30

Leu Met Thr Val Gly Lys Glu Pro Phe Pro Thr Ile Tyr Val Asp Ser
        35                  40                  45

Gln Lys Glu Asn Glu Arg Trp Asn Val Ile Ser Lys Ser Gln Leu Lys
50                  55                  60

Asn Ile Lys Lys Met Trp His Arg Glu Gln Met Lys Ser Glu Ser Arg
65                  70                  75                  80

Glu Lys Lys Glu Ala Glu Asp Ser Leu Arg Arg Glu Lys Asn Leu Glu
                85                  90                  95

Glu Ala Lys Lys Ile Thr Ile Lys Asn Asp Pro Ser Leu Pro Glu Pro
            100                 105                 110

Lys Cys Val Lys Ile Gly Ala Leu Glu Gly Tyr Arg Gly Gln Arg Val
        115                 120                 125

Lys Val Phe Gly Trp Val His Arg Leu Arg Arg Gln Gly Lys Asn Leu
130                 135                 140

Met Phe Leu Val Leu Arg Asp Gly Thr Gly Tyr Leu Gln Cys Val Leu
145                 150                 155                 160

Ala Asp Glu Leu Cys Gln Cys Tyr Asn Gly Val Leu Leu Ser Thr Glu
                165                 170                 175

Ser Ser Val Ala Val Tyr Gly Met Leu Asn Leu Thr Pro Lys Gly Lys
            180                 185                 190

Gln Ala Pro Gly Gly His Glu Leu Ser Cys Asp Phe Trp Glu Leu Ile
        195                 200                 205

Gly Leu Ala Pro Ala Gly Gly Ala Asp Asn Leu Ile Asn Glu Glu Ser
210                 215                 220

Asp Val Asp Val Gln Leu Asn Asn Arg His Met Met Ile Arg Gly Glu
225                 230                 235                 240

Asn Met Ser Lys Ile Leu Lys Ala Arg Ser Met Val Thr Arg Cys Phe
                245                 250                 255

Arg Asp His Phe Phe Asp Arg Gly Tyr Tyr Glu Val Thr Pro Pro Thr
            260                 265                 270

Leu Val Gln Thr Gln Val Glu Gly Gly Ala Thr Leu Phe Lys Leu Asp
        275                 280                 285

Tyr Phe Gly Glu Glu Ala Phe Leu Thr Gln Ser Ser Gln Leu Tyr Leu
290                 295                 300

Glu Thr Cys Leu Pro Ala Leu Gly Asp Val Phe Cys Ile Ala Gln Ser
305                 310                 315                 320
```

```
Tyr Arg Ala Glu Gln Ser Arg Thr Arg Arg His Leu Ala Glu Tyr Thr
                325                 330                 335

His Val Glu Ala Glu Cys Pro Phe Leu Thr Phe Asp Asp Leu Leu Asn
            340                 345                 350

Arg Leu Glu Asp Leu Val Cys Asp Val Val Asp Arg Ile Leu Lys Ser
        355                 360                 365

Pro Ala Gly Ser Ile Val His Glu Leu Asn Pro Asn Phe Gln Pro Pro
    370                 375                 380

Lys Arg Pro Phe Lys Arg Met Asn Tyr Ser Asp Ala Ile Val Trp Leu
385                 390                 395                 400

Lys Glu His Asp Val Lys Lys Glu Asp Gly Thr Phe Tyr Glu Phe Gly
                405                 410                 415

Glu Asp Ile Pro Glu Ala Pro Glu Arg Leu Met Thr Asp Thr Ile Asn
            420                 425                 430

Glu Pro Ile Leu Leu Cys Arg Phe Pro Val Glu Ile Lys Ser Phe Tyr
        435                 440                 445

Met Gln Arg Cys Pro Glu Asp Ser Arg Leu Thr Glu Ser Val Asp Val
    450                 455                 460

Leu Met Pro Asn Val Gly Glu Ile Val Gly Ser Met Arg Ile Phe
465                 470                 475                 480

Asp Ser Glu Glu Ile Leu Ala Gly Tyr Lys Arg Glu Gly Ile Asp Pro
                485                 490                 495

Thr Pro Tyr Tyr Trp Tyr Thr Asp Gln Arg Lys Tyr Gly Thr Cys Pro
            500                 505                 510

His Gly Gly Tyr Gly Leu Gly Leu Glu Arg Phe Leu Thr Trp Ile Leu
        515                 520                 525

Asn Arg Tyr His Ile Arg Asp Val Cys Leu Tyr Pro Arg Phe Val Gln
    530                 535                 540

Arg Cys Thr Pro
545

<210> SEQ ID NO 4
<211> LENGTH: 471
<212> TYPE: PRT
<213> ORGANISM: Homo sapiens

<400> SEQUENCE: 4

Met Pro Asn Ser Glu Pro Ala Ser Leu Leu Glu Leu Phe Asn Ser Ile
1               5                   10                  15

Ala Thr Gln Gly Glu Leu Val Arg Ser Leu Lys Ala Gly Asn Ala Ser
            20                  25                  30

Lys Asp Glu Ile Asp Ser Ala Val Lys Met Leu Val Ser Leu Lys Met
        35                  40                  45

Ser Tyr Lys Ala Ala Gly Glu Asp Tyr Lys Ala Asp Cys Pro Pro
    50                  55                  60

Gly Asn Pro Ala Pro Thr Ser Asn His Gly Pro Asp Ala Thr Glu Ala
65                  70                  75                  80

Glu Glu Asp Phe Val Asp Pro Trp Thr Val Gln Thr Ser Ser Ala Lys
                85                  90                  95

Gly Ile Asp Tyr Asp Lys Leu Ile Val Arg Phe Gly Ser Ser Lys Ile
            100                 105                 110

Asp Lys Glu Leu Ile Asn Arg Ile Glu Arg Ala Thr Gly Gln Arg Pro
        115                 120                 125

His His Phe Leu Arg Arg Gly Ile Phe Phe Ser His Arg Asp Met Asn
    130                 135                 140
```

| Gln | Val | Leu | Asp | Ala | Tyr | Glu | Asn | Lys | Lys | Pro | Phe | Tyr | Leu | Tyr | Thr |
| 145 | | | | | 150 | | | | | 155 | | | | | 160 |

| Gly | Arg | Gly | Pro | Ser | Ser | Glu | Ala | Met | His | Val | Gly | His | Leu | Ile | Pro |
| | | | | 165 | | | | | 170 | | | | | 175 | |

| Phe | Ile | Phe | Thr | Lys | Trp | Leu | Gln | Asp | Val | Phe | Asn | Val | Pro | Leu | Val |
| | | | 180 | | | | | 185 | | | | | 190 | | |

| Ile | Gln | Met | Thr | Asp | Asp | Glu | Lys | Tyr | Leu | Trp | Lys | Asp | Leu | Thr | Leu |
| | | | 195 | | | | | 200 | | | | | 205 | | |

| Asp | Gln | Ala | Tyr | Gly | Asp | Ala | Val | Glu | Asn | Ala | Lys | Asp | Ile | Ile | Ala |
| | | 210 | | | | | 215 | | | | | 220 | | | |

| Cys | Gly | Phe | Asp | Ile | Asn | Lys | Thr | Phe | Ile | Phe | Ser | Asp | Leu | Asp | Tyr |
| 225 | | | | | 230 | | | | | 235 | | | | | 240 |

| Met | Gly | Met | Ser | Ser | Gly | Phe | Tyr | Lys | Asn | Val | Val | Lys | Ile | Gln | Lys |
| | | | | 245 | | | | | 250 | | | | | 255 | |

| His | Val | Thr | Phe | Asn | Gln | Val | Lys | Gly | Ile | Phe | Gly | Phe | Thr | Asp | Ser |
| | | | 260 | | | | | 265 | | | | | 270 | | |

| Asp | Cys | Ile | Gly | Lys | Ile | Ser | Phe | Pro | Ala | Ile | Gln | Ala | Ala | Pro | Ser |
| | | 275 | | | | | 280 | | | | | 285 | | | |

| Phe | Ser | Asn | Ser | Phe | Pro | Gln | Ile | Phe | Arg | Asp | Arg | Thr | Asp | Ile | Gln |
| | 290 | | | | | 295 | | | | | 300 | | | | |

| Cys | Leu | Ile | Pro | Cys | Ala | Ile | Asp | Gln | Asp | Pro | Tyr | Phe | Arg | Met | Thr |
| 305 | | | | | 310 | | | | | 315 | | | | | 320 |

| Arg | Asp | Val | Ala | Pro | Arg | Ile | Gly | Tyr | Pro | Lys | Pro | Ala | Leu | Leu | His |
| | | | | 325 | | | | | 330 | | | | | 335 | |

| Ser | Thr | Phe | Phe | Pro | Ala | Leu | Gln | Gly | Ala | Gln | Thr | Lys | Met | Ser | Ala |
| | | | 340 | | | | | 345 | | | | | 350 | | |

| Ser | Asp | Pro | Asn | Ser | Ser | Ile | Phe | Leu | Thr | Asp | Thr | Ala | Lys | Gln | Ile |
| | | 355 | | | | | 360 | | | | | 365 | | | |

| Lys | Thr | Lys | Val | Asn | Lys | His | Ala | Phe | Ser | Gly | Gly | Arg | Asp | Thr | Ile |
| | 370 | | | | | 375 | | | | | 380 | | | | |

| Glu | Glu | His | Arg | Gln | Phe | Gly | Gly | Asn | Cys | Asp | Val | Asp | Val | Ser | Phe |
| 385 | | | | | 390 | | | | | 395 | | | | | 400 |

| Met | Tyr | Leu | Thr | Phe | Phe | Leu | Glu | Asp | Asp | Lys | Leu | Glu | Gln | Ile |
| | | | | 405 | | | | | 410 | | | | | 415 |

| Arg | Lys | Asp | Tyr | Thr | Ser | Gly | Ala | Met | Leu | Thr | Gly | Glu | Leu | Lys | Lys |
| | | | 420 | | | | | 425 | | | | | 430 | | |

| Ala | Leu | Ile | Glu | Val | Leu | Gln | Pro | Leu | Ile | Ala | Glu | His | Gln | Ala | Arg |
| | | 435 | | | | | 440 | | | | | 445 | | | |

| Arg | Lys | Glu | Val | Thr | Asp | Glu | Ile | Val | Lys | Glu | Phe | Met | Thr | Pro | Arg |
| | 450 | | | | | 455 | | | | | 460 | | | | |

| Lys | Leu | Ser | Phe | Asp | Phe | Gln |
| 465 | | | | 470 | | |

<210> SEQ ID NO 5
<211> LENGTH: 2907
<212> TYPE: DNA
<213> ORGANISM: Artificial Sequence
<220> FEATURE:
<223> OTHER INFORMATION: ARS coding sequence

<400> SEQUENCE: 5

```
atggactcta ctctaacagc aagtgaaatc cggcagcgat ttatagattt cttcaagagg      60
aacgagcata cgtatgttca ctcgtctgcc accatcccat ggatgacccc cactttgctc     120
tttgccaatg caggcatgaa ccagtttaaa cccattttcc tgaacacaat tgacccatct     180
caccccatgg caaagctgag cagagctgcc aatacccaga agtgcatccg ggctgggggc     240
```

```
aaacaaaatg acctggacga tgtgggcaag gatgtctatc atcacacctt cttcgagatg    300
ctgggctctt ggtcttttgg agattacttt aaggaattgg catgtaagat ggctctggaa    360
ctcctcaccc aagagtttgg cattcccatt gaaagacttt atgttactta ctttggcggg    420
gatgaagcag ctggcttaga agcagatctg gaatgcaaac agatctggca aaatttgggg    480
ctggatgaca ccaaaatcct cccaggcaac atgaaggata acttctggga gatgggtgac    540
acgggcccct gtggtccttg cagtgagatc cactacgacc ggattggtgg tcgggacgcc    600
gcacatcttg tcaaccagga cgaccctaat gtgctggaga tctggaacct tgtgttcatc    660
cagtataaca gggaagctga tggcattctg aaacctcttc ccaagaaaag cattgacaca    720
gggatgggcc tggaacgact ggtatctgtg ctgcagaata gatgtccaa ctatgacact    780 gacctttttg tcccttactt tgaagccatt cagaagggca caggtgcccg accatacact    840
gggaaagttg gtgctgagga tgccgatggg attgacatgg cctaccgggt gctggctgac    900
catgctcgga ccatcactgt ggcactggct gatggtggcc ggcctgacaa cacagggcgt    960
ggatatgtgt tgagacggat tctccgccga gctgtccgat acgcccatga aaagctcaat   1020
gccagcaggg gcttctttgc tacgttagtg gatgttgtcg tccagtccct gggagatgca   1080
tttcctgagc tgaagaagga cccagacatg gtgaaggaca tcattaatga agaagaggtg   1140
cagtttctca agactctcag cagagggcgt cgcatcctgg acaggaaaat tcagagcctg   1200
ggagacagca agaccattcc cggagacact gcttggctcc tctatgacac ctatgggttt   1260
ccagtggatc tgactggact gattgctgaa gagaagggcc tggtggtaga catggatggc   1320
tttgaagagg agaggaaact ggcccagctg aaatcacagg caagggagc tggtggggaa   1380 gacctcatta tgctggacat ttacgctatc gaagagctcc gggcacgggg tctggaggtc   1440
acagatgatt ccccaaagta caattaccat ttggactcca gtggtagcta tgtatttgag   1500
aacacagtgg ctacggtgat ggctctgcgc agggagaaga tgttcgtgga agaggtgtcc   1560
acaggccagg agtgtggagt ggtgctggac aagacctgtt tctatgctga gcaaggaggc   1620
cagatctatg acgaaggcta cctggtgaag gtggatgaca gcagtgaaga taaaacagag   1680
tttacagtga agaatgctca ggtccgagga gggtatgtgc tacacattgg aaccatctac   1740
ggtgacctga agtggggga tcaggtctgg ctgtttattg atgagcccg acgaagaccc   1800 atcatgagca accacacagc tacgcacatt ctgaacttcg ccctgcgctc agtgcttggg   1860
gaagctgacc agaaaggctc attggttgct cctgaccgcc tcagatttga ctttactgcc   1920
aagggagcca tgtccaccca acagatcaag aaggctgaag agattgctaa tgagatgatt   1980
gaggcagcca aggccgtcta tacccaggat tgccccctgg cagcagcgaa agccatccag   2040
ggcctacggg ctgtgtttga tgagacctat cctgaccctg tgcgagtcgt tccattggg   2100 gtcccggtgt ccgagttgct ggatgacccc tctgggcctg ctggctccct gacttctgtt   2160
gagttctgtg ggggaacgca cctgcggaac tcgagtcatg caggagcttt tgtgatcgtg   2220
acggaagaag ccattgccaa gggtatccgg aggattgtgg ctgtcacagg tgccgaggcc   2280
cagaaggccc tcaggaaagc agagagcttg aagaaatgtc tctctgtcat ggaagccaaa   2340
gtgaaggctc agactgctcc aaacaaggat gtgcagaggg agatcgctga ccttggagag   2400
gccctggcca ctgcagtcat cccccagtgg cagaaggatg aattgcggga gactctcaaa   2460
tccctaaaga aggtcatgga tgacttggac cgagccagca agccgatgt ccagaaacga   2520 gtgttagaga agacgaagca gttcatcgac agcaaccca accagcctct tgtcatcctg   2580
gagatggaga gcggcgccctc agccaaggcc ctgaatgaag ccttgaagct cttcaagatg   2640
```

| | |
|---|---|
| cactcccctc agacttctgc catgctcttc acggtggaca atgaggctgg caagatcacg | 2700 |
| tgcctgtgtc aagtccccca gaatgcagcc aatcggggct taaaagccag cgagtgggtg | 2760 |
| cagcaggtgt caggcttgat ggacggtaaa ggtggtggca aggatgtgtc tgcacaggcc | 2820 |
| acaggcaaga acgttggctg cctgcaggag gcgctgcagc tggccacttc cttcgcccag | 2880 |
| ctgcgcctcg gggatgtaaa gaactga | 2907 |

<210> SEQ ID NO 6
<211> LENGTH: 2058
<212> TYPE: DNA
<213> ORGANISM: Artificial Sequence
<220> FEATURE:
<223> OTHER INFORMATION: GRS coding sequence

<400> SEQUENCE: 6

| | |
|---|---|
| atggacggcg cgggggctga ggaggtgctg gctcctctga ggctagcagt gcgccagcag | 60 |
| ggagatcttg tgcgaaaact caaagaagat aaagcacccc aagtagacgt agacaaagca | 120 |
| gtggctgagc tcaaagcccg caagagggtt ctggaagcaa aggagctggc gttacagccc | 180 |
| aaagatgata ttgtagaccg agcaaaaatg aagataccc tgaaggaggag gttttctat | 240 |
| gatcaagctt ttgctattta tggaggtgtt agtggtctgt atgactttgg gccagttggc | 300 |
| tgtgctttga gaacaatat tattcagacc tggaggcagc actttatcca agaggaacag | 360 |
| atcctggaga tcgattgcac catgctcacc cctgagccag ttttaaagac ctctggccat | 420 |
| gtagacaaat ttgctgactt catggtgaaa gacgtaaaaa atggagaatg ttttcgtgct | 480 |
| gaccatctat aaaagctca tttacagaaa ttgatgtctg ataagaagtg ttctgtcgaa | 540 |
| aagaaatcag aaatggaaag tgttttggcc cagcttgata actatggaca gcaagaactt | 600 |
| gcggatcttt ttgtgaacta taatgtaaaa tctcccatta ctggaaatga tctatcccct | 660 |
| ccagtgtctt ttaacttaat gttcaagact ttcattgggc tggaggaaa catgcctggg | 720 |
| tacttgagac cagaaactgc acaggggatt ttcttgaatt tcaaacgact tttggagttc | 780 |
| aaccaaggaa agttgccttt tgctgctgcc cagattggaa attcttttag aaatgagatc | 840 |
| tcccctcgat ctggactgat cagagtcaga gaattcacaa tggcagaaat tgagcacttt | 900 |
| gtagatccca gtgagaaaga ccaccccaag ttccagaatg tggcagacct tcacctttat | 960 |
| ttgtattcag caaaagccca ggtcagcgga cagtccgctc ggaaaatgcg cctgggagat | 1020 |
| gctgttgaac agggtgtgat taataacaca gtattaggct atttcattgg ccgcatctac | 1080 |
| ctctacctca cgaaggttgg aatatctcca gataaactcc gcttccggca gcacatggag | 1140 |
| aatgagatgg cccattatgc ctgtgactgt gggatgcag aatccaaaac atcctacggt | 1200 |
| tggattgaga ttgttggatg tgctgatcgt tcctgttatg acctctcctg tcatgcacga | 1260 |
| gccaccaaag tcccacttgt agctgagaaa cctctgaaag aacccaaaac agtcaatgtt | 1320 |
| gttcagtttg aacccagtaa gggagcaatt ggtaaggcat ataagaagga tgcaaaactg | 1380 |
| gtgatggagt atcttgccat ttgtgatgag tgctacatta cagaaattga gatgctgctg | 1440 |
| aatgagaaag gggaattcac aattgaaact gaagggaaaa catttcagtt aacaaaagac | 1500 |
| atgatcaatg tgaagagatt ccagaaaaca ctatatgtgg aagaagttgt tccgaatgta | 1560 |
| attgaacctt ccttcggcct gggtaggatc atgtatacgg tatttgaaca tacattccat | 1620 |
| gtacgagaag gagatgaaca gagaacattc ttcagtttcc ctgctgtagt tgctccattc | 1680 |
| aaatgttccg tcctcccact gagccaaaac caggagttca tgccatttgt caaggaatta | 1740 |
| tcggaagccc tgaccaggca tggagtatct cacaaagtag acgattcctc tgggtcaatc | 1800 |

```
ggaaggcgct atgccaggac tgatgagatt ggcgtggctt ttggtgtcac cattgacttt    1860
gacacagtga acaagacccc ccacactgca actctgaggg accgtgactc aatgcggcag    1920
ataagagcag agatctctga gctgcccagc atagtccaag acctagccaa tggcaacatc    1980
acatgggctg atgtggaggc caggtatcct ctgtttgaag ggcaagagac tggtaaaaaa    2040
gagacaatcg aggaatga                                                  2058
```

<210> SEQ ID NO 7
<211> LENGTH: 1647
<212> TYPE: DNA
<213> ORGANISM: Artificial Sequence
<220> FEATURE:
<223> OTHER INFORMATION: NRS coding sequence

<400> SEQUENCE: 7

```
atggtgctag cagagctgta cgtctctgac cgagagggaa gcgatgccac gggagatgga     60
accaaggaga aacatttaa  acaggtctaa aggctttga  tgacagtagg gaaagaacca    120
tttcctacca tttacgtaga ttcacaaaaa gaaatgagag gtggaatgt  tatttctaaa    180 tcacagttga agaacattaa aaagatgtgg catagggaac aaatgaagag tgaatcccgg    240
gaaaagaaag aggcagaaga tagtttacga agagaaaaga acctggaaga agcaaagaag    300
attaccatta aaaatgatcc aagtctccca gagccaaaat gtgtgaagat tggtgcgtta    360
gaaggatata gaggccaaag agtaaaggtg tttggctggg tccacaggct cgcaggcaa    420 ggaaagaatt taatgtttct ggtgttgcga atggtacag  ttatcttca  gtgtgtcttg    480 gcggatgagt tgtgtcagtg ctacaatgga gttctcttgt ccacggagag cagtgttgca    540
gtgtatggaa tgctaaatct tacccccaaag ggcaagcagg ctccaggtgg ccatgagctg    600
agttgtgact tctgggaact aattgggttg ccccctgctg gaggagctga caacctgatc    660
aatgaggagt ctgacgttga tgtccagctc aacaacagac acatgatgat ccgaggagaa    720
aacatgtcca aaatcctaaa agcacgatcc atggtcacca ggtgctttag agatcacttc    780
tttgataggg gtactatgag agttactcct ccaacattag tgcaaacaca gtagaaggt    840 ggtgccacac tcttcaagct tgactatttt ggggaagagg cattttttgac tcaatcctct    900 cagttgtact ggagacctg  cctcccagcc ctgggagatg ttttttgtat tgctcagtca    960
taccgggcag agcagtccag aacacgaagg cacctggctg agtacactca cgtggaagct   1020
gagtgtcctt tcctgacttt tgacgacctc ctgaaccggt tggaggactt ggtttgtgat   1080
gtggtagatc gaatattgaa gtcacctgca gggagcatag tgcatgagct caaccccgaac   1140 tttcagcccc ccaaacggcc tttcaaacgg atgaactatt cagatgctat cgtttggcta   1200
aaagaacatg atgtaaagaa agaagatgga actttctatg aatttggaga agatatccca   1260
gaagctcctg agagactgat gacagacacc attaatgaac caatcttgct gtgtcgattt   1320
cctgtggaga tcaagtcctt ctacatgcag cgatgtcctg aggattcccg tcttactgaa   1380
tctgtcgacg tgttgatgcc caatgttggt gagattgtgg aggctcaat  gcgtatcttt   1440 gatagtgaag aaatactggc aggttataaa agggaaggga ttgaccccac tccctattac   1500
tggtatacgg atcagagaaa atacggtaca tgtccccatg gaggatatgg cttgggcttg   1560
gaacgattct taacgtggat tctgaatagg tatcacatcc gagacgtgtg cttatacct   1620 cgatttgtcc agcgttgcac gccataa                                        1647
```

<210> SEQ ID NO 8
<211> LENGTH: 1416

<212> TYPE: DNA
<213> ORGANISM: Artificial Sequence
<220> FEATURE:
<223> OTHER INFORMATION: WRS coding sequence

<400> SEQUENCE: 8

```
atgcccaaca gtgagcccgc atctctgctg gagctgttca acagcatcgc cacacaaggg      60
gagctcgtaa ggtccctcaa agcgggaaat gcgtcaaagg atgaaattga ttctgcagta     120
aagatgttgg tgtcattaaa aatgagctac aaagctgccg cggggagga ttacaaggct      180
gactgtcctc cagggaaccc agcacctacc agtaatcatg cccagatgc cacagaagct      240
gaagaggatt ttgtggaccc atggacagta cagacaagca gtgcaaaagg catagactac     300
gataagctca ttgttcggtt tggaagtagt aaaattgaca aagagctaat aaaccgaata     360
gagagagcca ccggccaaag accacaccac ttcctgcgca gaggcatctt cttctcacac     420
agatatga atcaggttct tgatgcctat gaaaataaga agccatttta tctgtacacg       480
ggccggggcc cctcttctga agcaatgcat gtaggtcacc tcattccatt tattttcaca     540
aagtggctcc aggatgtatt taacgtgccc ttggtcatcc agatgacgga tgacgagaag     600
tatctgtgga aggacctgac cctggaccag gcctatggcg atgctgttga aatgccaag      660
gacatcatcg cctgtggctt tgacatcaac aagactttca tattctctga cctggactac     720
atggggatga gctcaggttt ctacaaaaat gtggtgaaga ttcaaaagca tgttaccttc     780
aaccaagtga aaggcatttt cggcttcact gacagcgact gcattgggaa gatcagtttt     840
cctgccatcc aggctgctcc ctccttcagc aactcattcc acagatcttc cgagacagg     900
acggatatcc agtgccttat cccatgtgcc attgaccagg atccttactt tagaatgaca     960
agggacgtcg cccccaggat cggctatcct aaaccagccc tgttgcactc caccttcttc    1020
ccagccctgc agggcgccca gaccaaaatg agtgccagcg acccaaactc ctccatcttc    1080
ctcaccgaca cggccaagca gatcaaaacc aaggtcaata agcatgcgtt ttctggaggg    1140
agagacacca tcgaggagca caggcagttt gggggcaact gtgatgtgga cgtgtctttc    1200
atgtacctga ccttcttcct cgaggacgac gacaagctcg agcagatcag gaaggattac    1260
accagcggag ccatgctcac cggtgagctc aagaaggcac tcatagaggt tctgcagccc    1320
ttgatcgcag agcaccaggc ccggcgcaag gaggtcacgg atgagatagt gaaagagttc    1380
atgactcccc ggaagctgtc cttcgacttt cagtag                              1416
```

DIAGNOSTIC MARKER FOR TYPE 1 DIABETES MELLITUS

TECHNICAL FIELD

The present invention relates to a novel diagnostic marker for type 1 diabetes mellitus. More particularly the present invention relates to a diagnostic composition for type 1 diabetes mellitus comprising an aminoacyl tRNA synthetase or an antibody thereto, as an active ingredient, the use of the aminoacyl tRNA synthetase for preparing an agent for diagnosing of type 1 diabetes mellitus, and a method for diagnosing type 1 diabetes mellitus by detecting an anti-alanyl tRNA synthetase antibody, an anti-glycyl tRNA synthetase antibody, an anti-asparaginyl tRNA synthetase antibody, and an anti-tryptophanyl tRNA synthetase antibody, from an individual test sample.

BACKGROUND OF THE ART

Diabetes mellitus may be divided into type 1 diabetes mellitus and Type 2 diabetes mellitus. Type 1 diabetes mellitus is an autoimmune disease in which genetic susceptibility and virus infection cause immunological responses in a pancreas, and β-cells are selectively destroyed. Type 2 diabetes mellitus is preceded by insulin resistance, and has been reported to be caused by complicated factors such as obesity, reduction of insulin receptor, reduction of tyrosine kinase activity, reduction of muscle/adipose tissue type transporter in a muscle tissue and an adipose tissue, and intracellular deficiency of insulin receptor substrate-1(IRS-1).

Especially, type 1 diabetes mellitus is known to be one of typical autoimmune diseases, and is a chronic disease in which pancreas β-cells-recognizable auto-activating T cells destroy insulin-producing pancreas β-cells. Humoral and cellular immune responses are mainly related to type 1 diabetes mellitus, and an autoantibody against various islet cell antibodies exists in the plasma of type 1 diabetes mellitus patients. Autoantibodies, against glutamate decarboxylase (GAD65), insulin, and protein tyrosine phosphatase-related islet antibodies 2 (IA-2), are used together with HbA1C and c-peptide quantification, to diagnose type 1 diabetes mellitus. Early diagnosis and exact determination allow medical treatment to be carried out at an early stage, and then is useful in delaying the progress of type 1 diabetes mellitus. Thus, they are clinically important. In the use of an autoantibody diagnosis, anti-GAD65 antibody showed a sensitivity of about 60 to 80%, anti-insulin antibody showed 40 to 60%, and anti-IA-2 antibody showed 30 to 70%. Even when three autoantibodies are combined, only 80 to 90% of type 1 diabetes mellitus can be covered. Accordingly, it has been required to develop a novel autoantibody diagnosis method for early diagnosis of type 1 diabetes mellitus.

DISCLOSURE

Technical Problem

Accordingly, the inventors of the present invention researched physiological functions of an aminoacyl tRNA synthetase. Then, they found that a lot of autoantibodies against the synthetase exist in type 1 diabetes mellitus patients, and can be detected by the aminoacyl tRNA synthetase. Thus, they completed the present invention by developing a diagnostic composition for type 1 diabetes mellitus comprising the aminoacyl tRNA synthetase.

Accordingly, an object of the present invention is to provide a novel use of an aminoacyl tRNA synthetase.

Technical Solution

In order to accomplish the object, the present invention provides a diagnostic composition for type 1 diabetes mellitus comprising aminoacyl tRNA synthetase.

In order to accomplish another object, the present invention provides a diagnostic kit for type 1 diabetes mellitus comprising the composition.

In order to accomplish still another object, the present invention provides a method detecting one or more antibody selected from the group consisting of anti-ARS antibody, anti-GRS antibody, anti-NRS antibody and anti-WRS antibody to provide information for diagnosis of type 1 diabetes mellitus through antigen-antibody reaction of patient's test sample.

In order to accomplish still another object, the present invention provides the use of aminoacyl tRNA synthetase selected from the group consisting of alanyl tRNA synthetase, glycyl tRNA synthetase, asparaginyl tRNA synthetase and tryptophanyl tRNA synthetase for preparing a reagent for diagnosis of type 1 diabetes mellitus.

In order to accomplish still another object, the present invention provides a method for diagnosis of type 1 diabetes mellitus comprising a step of detecting an anti-alanyl tRNA synthetase antibody, an anti-glycyl tRNA synthetase antibody, an anti-asparaginyl tRNA synthetase antibody, and an anti-tryptophanyl tRNA synthetase antibody, from an individual test sample.

Hereinafter, exemplary embodiments will be described in detail with reference to the accompanying drawings.

A composition of the present invention comprises aminoacyl tRNA synthetase and may be used for diagnosis of type 1 diabetes mellitus.

Aminoacyl tRNA synthetase of the present invention is a protein catalyzing binding of corresponding tRNA and aminoacyl tRNA synthetases of the present invention preferably may be alanyl tRNA synthetase, glycyl tRNA synthetase, asparaginyl tRNA synthetase and tryptophanyl tRNA synthetase alone or in combination.

The alanyl tRNA synthetase, glycyl tRNA synthetase, asparaginyl tRNA synthetase and tryptophanyl tRNA synthetase may be, but not limited thereto, the polypeptide represented by the SEQ ID NO: 1 (ARS), SEQ ID NO: 2 (GRS), SEQ ID NO: 3 (NRS) and SEQ ID NO: 4 (WRS) respectively. In addition, alanyl tRNA synthetase may be the sequence described in Genbank Accession No. D32050, glycyl tRNA synthetase may be the sequence described in Genbank Accession No. U9510, asparaginyl tRNA synthetase may be the sequence described in Genbank Accession No. D84273 and tryptophanyl tRNA synthetase may be the sequence described in Genbank Accession No. M61715. In addition, the alanyl tRNA synthetase, the glycyl tRNA synthetase, the asparaginyl tRNA synthetase and the tryptophanyl tRNA synthetase comprise functional equivalent thereof.

The term "functional equivalents" refers to polypeptide comprising the amino acid sequence having at least 70% amino acid sequence homology (i.e., identity), preferably at least 80%, and more preferably at least 90%, for example, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and 100% amino acid sequence homology, that exhibit substantially identical physiological activity to individual aminoacyl tRNA synthetase (i.e. ARS, GRS, NRS or WRS). The "substantially identical physiological activity" means a polypeptide showing activity of individual aminoacyl tRNA synthetase. The functional equivalents may include, for example peptides produced by as a result of addition, substitution or deletion of some amino acid of the polypeptide of SEQ ID NO: 1, SEQ ID NO: 2, SEQ ID NO: 3 or SEQ ID NO: 4. Substitutions of the amino acids are preferably conservative substitutions. Examples of conservative substitutions of naturally occurring amino acids are as follows: aliphatic amino acids (Gly, Ala, Pro), hydrophobic amino acids (Ile, Leu, Val), aromatic amino acids (Phe, Tyr, Trp), acidic amino acids (Asp, Glu), basic amino acids (His, Lys, Arg, Gln, Asn) and sulfur-containing amino acids (Cys, Met). Furthermore, the functional equivalents also include variants with deletion of some of the amino acid sequence of the aminoacyl tRNA synthetase. Deletion or substitutions of the amino acids are preferably located at regions that are not directly involved in the physiological activity of the aminoacyl tRNA synthetase. And deletion of the amino acids is preferably located at regions that are not directly involved in the physiological activity of aminoacyl tRNA synthetase. In addition, the functional equivalents also include variants with addition of several amino acids in both terminal ends of the amino acid sequence of the aminoacyl tRNA synthetase or in the sequence. Moreover, the inventive functional equivalents also include polypeptide derivatives which have modification of some of the chemical structure of the inventive polypeptide while maintaining the fundamental backbone and physiological activity of the inventive polypeptide. Examples of this modification include structural modifications for changing the stability, storage, volatility or solubility of the inventive polypeptide.

Sequence identity or homology is defined herein as the percentage of amino acid residues in the candidate sequence that are identical with amino acid sequence of ARS, GRS, NRS or WRS, after aligning the sequences and introducing gaps, if necessary, to achieve the maximum percent sequence identity, and not considering any conservative substitutions (as described above) as part of the sequence identity. None of N-terminal, C-terminal, or internal extensions, deletions, or insertions into the amino acid sequence of ARS, GRS, NRS or WRS shall be construed as affecting sequence identity or homology. Thus, sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences or along a predetermined portion of one or both sequences). The programs provide a default opening penalty and a default gap penalty, and a scoring matrix such as PAM 250 (a standard scoring matrix; see Dayhoff et al., in Atlas of Protein Sequence and Structure, vol. 5, supp. 3 (1978)) can be used in conjunction with the computer program. For example, the percent identity can be calculated as the follow. The total number of identical matches multiplied by 100 and then divided by the sum of the length of the longer sequence within the matched span and the number of gaps introduced into the longer sequences in order to align the two sequences.

ARS, GRS, NRS or WRS of the present invention can be prepared by separating from nature materials or genetic engineering methods. For example, ARS, GRS, NRS or WRS or its functional equivalents is constructed according to any conventional method. The DNA molecule may synthesize by performing PCR using suitable primers. Alternatively, the DNA molecule may also be synthesized by a standard method known in the art, for example using an automatic DNA synthesizer (commercially available from Biosearch or Applied Biosystems). The constructed DNA molecule is inserted into a vector comprising at least one expression control sequence (ex: promoter, enhancer) that is operatively linked to the DNA sequence so as to control the expression of the DNA molecule, and host cells are transformed with the resulting recombinant expression vector. The transformed cells are cultured in a medium and condition suitable to express the DNA sequence, and a substantially pure polypeptide encoded by the DNA sequence is collected from the culture medium. The collection of the pure polypeptide may be performed using a method known in the art, for example, chromatography. In this regard, the term "substantially pure polypeptide" means the inventive polypeptide that does not substantially contain any other proteins derived from host cells. For the genetic engineering method for synthesizing the inventive polypeptide, the reader may refer to the following literatures: Maniatis et al., Molecular Cloning: A Laboratory Manual, Cold Spring Harbor Laboratory 1982; Sambrook et al., Molecular Cloning; A Laboratory Manual, Cold Spring Harbor Press, N.Y., Second (1998) and Third (2000) Editions; Gene Expression Technology, Method in Enzymology, Genetics and Molecular Biology, Method in Enzymology, Guthrie & Fink (eds.), Academic Press, San Diego, Calif. 1991; and Hitzeman et al., J. Biol. Chem., 255, 12073-12080, 1990.

Alternatively, ARS, GRS, NRS or WRS of the present invention can be chemically synthesized easily according to any technique known in the art (Creighton, Proteins: Structures and Molecular Principles, W.H. Freeman and Co., NY, 1983). As a typical technique, they are not limited to, but include liquid or solid phase synthesis, fragment condensation, F-MOC or T-BOC chemistry (Chemical Approaches to the Synthesis of Peptides and Proteins, Williams et al., Eds., CRC Press, Boca Raton Fla., 1997; A Practical Approach, Atherton & Sheppard, Eds., IRL Press, Oxford, England, 1989).

Meanwhile, the present invention provides a diagnostic composition for type 1 diabetes mellitus comprising one or more of ARS, GRS, NRS or WRS.

The kit of the present invention may comprise an instrument and/or an agent for immunological analysis which is well known in the art as well as ARS, GRS, NRS or WRS.

The immunological analysis may comprise a method as long as it can measure binding of antigen-antibody. These methods are well known in the art and for example, there are immunocytochemistry and immunohistochemistry, radioimmunoassays, ELISA (Enzyme Linked Immunoabsorbent assay), immunoblotting, Farr assay, immunoprecipitation, latex cohesion, erythrocyte cohesion, nephelometry, immunodiffusion, count-current electrophoresis, single radical immunodiffusion, protein chip and immunofluorescence.

As an instrument and/or a reagent for immunological analysis, it comprises a suitable carrier or a support, a marker which produces a detectable signal, a diluents and a cleansing agent. In addition, when the marker is an enzyme, it may comprise a substrate which enables to measure activity of the enzyme and a reaction blocking agent.

ARS, GRS, NRS or WRS which is included in the diagnostic kit of the present invention preferably may be fixed to a suitable carrier or a support as disclosed in the reference (Antibodies: A Laboratory Manual, Harlow & Lane, Cold Spring Harbor, 1988). As examples of a suitable carrier or a support, there are agarose, cellulose, nitrocellulose, dextran, sephadex, sepharose, liposome, carboxymethylcellulose, polyacrylamide, polysterine, gabbro, filter paper, ion exchange resin, plastic film, plastic tube, glass, polyaminemethylvinyl-ether-maleic acid copolymer, amino acid copolymer, ethylene-maleic acid copolymer, nylon, cup, flat packs. As other solid substrates, there are a cell culture plate, an ELISA plate, a tube and a polymeric membrane. The support may have a random form, for example, a form of globular (beads), cylindrical (test tube or inside of well), plane (sheet, test strip).

A marker which produces a detectable signal enables to measure formation of antigen-antibody complex qualitatively and quantitatively and the examples are an enzyme, a fluorescent material, a ligand, a luminous material, microparticle, a redox molecule and a radioactive isotope. As an enzyme, β-glucuronidase, β-D-glucosidase, urase, peroxidase, alkaline phosphatase, acetylcholine esterase, glucose oxidase, hexokinase, malate dehydrogenase, glucose-6-phosphate hydrogenase or invertase may be used. As a fluorescent material, fluorescin, isothiocyanate, rodamin, phycoerythrin, phycocyanin, allophycocyanin or fluorescinisothiocyanate may be used. As a ligand, there are biotin derivatives and as a luminous material, acridium, ester, luciferin and luciferase. As a microparticle, there are colloid gold and colored latex, and as a redox molecule, there are ferrocene, ruthenium complex compound, biologen, quinone, Ti ion, Cs ion, dimide, 1,4-benzoquinone and hydroquinone. As a radioactive isotope, $^3H$, $^{14}C$, $^{32}P$, $^{35}S$, $^{36}Cl$, $^{51}Co$, $^{58}Co$, $^{59}Fe$, $^{90}Y$, $^{125}I$, $^{131}I$ and $^{186}Re$. However, besides the above mentioned things, anything can be used as long as it can be used in immunological analysis.

Also, the diagnostic kit for type 1 diabetes mellitus may further comprise composition for detecting a marker for type 1 diabetes mellitus which is well known in the art. For example, a marker for type 1 diabetes mellitus which is well known in the art may be, but not limited thereto, anti-GAD65 antibody, anti-IA-2 antibody, anti-insulin antibody, anti-islet cell antigen (ICA) antibody, Hb1Ac, C-peptide, Slc30A8.

Also, to provide necessary information for diagnosis of type 1 diabetes mellitus, the present invention provides a method for detecting one or more antibody selected from the group consisting of anti-ARS antibody, anti-GRS antibody, anti-NRS antibody and anti-WRS antibody through antigen-antibody reaction from a sample of a patient. At this time, antigen-antibody reaction is well described above.

Above-mentioned anti-ARS antibody, anti-GRS antibody, anti-NRS antibody and anti-WRS antibody mean protein molecules specific to an epitope of ARS, GRS, NRS and WRS respectively. For the purpose of the present invention, the antibody means an antibody specifically binding to ARS, GRS, NRS or WRS respectively and preferably it is an autoantibody.

In addition, the antibodies of the present invention include complete forms having two full-length light chains and two full-length heavy chains, as well as functional fragments of antibody molecules. The functional fragments of antibody molecules refer to fragments retaining at least an antigen-binding function, and include Fab, F(ab'), F(ab')2 and Fv.

A composition of the present invention may comprise 0.01 to 99.99 weight % of one or more aminoacyl tRNA synthetase which is selected from the group consisting of alanyl tRNA synthetase, glycyl tRNA synthetase, asparaginyl tRNA synthetase, and tryptophanyl tRNA synthetase and the rest may be a carrier. Further, a composition of the present invention may comprise 0.01 to 99.99 weight % of one or more anti-aminoacyl tRNA synthetase antibody which is selected from the group consisting of an anti-alanyl tRNA synthetase antibody, an anti-glycyl tRNA synthetase antibody, an anti-asparaginyl tRNA synthetase antibody, and an anti-tryptophanyl tRNA synthetase antibody and the rest may be a carrier.

In addition, in the present invention, ARS, GRS, NRS and WRS may be a fragment which can bind to an anti-alanyl tRNA synthetase antibody, an anti-glycyl tRNA synthetase antibody, an anti-asparaginyl tRNA synthetase antibody, and an anti-tryptophanyl tRNA synthetase antibody as well as full length ARS, GRS, NRS and WRS.

In addition, the present invention provides the use of one or more aminoacyl tRNA synthetase which is selected from the group consisting of alanyl tRNA synthetase, glycyl tRNA synthetase, asparaginyl tRNA synthetase, and tryptophanyl tRNA synthetase for preparing a reagent for diagnosis of type 1 diabetes mellitus.

In order to accomplish still another object, the present invention provides a method for diagnosis of type 1 diabetes mellitus comprising a step of detecting an anti-alanyl tRNA synthetase antibody, an anti-glycyl tRNA synthetase antibody, an anti-asparaginyl tRNA synthetase antibody, and an anti-tryptophanyl tRNA synthetase antibody, from an individual test sample.

As used herein, the term "subject" means mammals, particularly animals including human beings. The subject may be patients in need of diagnosis.

As used herein, the term "biological sample" or "sample" comprises solid tissue samples such as biologically originated and liquefied samples, biopsy samples, and tissue culture or cells originated thereof. More specifically, for example, but not limited thereto, it may be tissue, extract, cell lysate, hole blood, blood plasma, serum, saliva, ocular humor, cerebrospinal fluid, sweat, urine, milk, ascites, synovial fluid and peritoneum fluid and preferably it may be serum or synovial fluid. The sample is acquired from animals, preferably from mammals and most preferably from human beings. The sample may be pretreated before use. For example, it may comprise filtration, distillation, extraction, concentration, inactivation of inhibitors, adding of a reagent. In addition, the protein may be isolated from the sample and used for detection.

For the genetic engineering method for nucleotides and proteins of the present invention, it may be referred to the following literatures: Maniatis et al., Molecular Cloning: A Laboratory Manual, Cold Spring Harbor Laboratory 1982; Sambrook et al., Molecular Cloning; A Laboratory Manual, Cold Spring Harbor Press, N.Y., Second (1998) and Third (2000) Editions; Gene Expression Technology, Method in Enzymology, Genetics and Molecular Biology, Method in Enzymology, Guthrie & Fink (eds.), Academic Press, San Diego, Calif. 1991; and Hitzeman et al., J. Biol. Chem., 255, 12073-12080 1990.

Further, regarding the type 1 diabetes mellitus, the below-mentioned are referred: Latent autoimmune (Type-1) diabetes mellitus in adults. Part. I. Serologic markers of autoimmune involvement of pancreatic beta-cells: GADA, ICA, IA-2 a IA-A. Martinka E, Ocen A, Strakov J, Mok M. Vnitr Lek. 1999 February; 45 (2):97-102; Prevalence of ICA and GAD antibodies at initial presentation of type 1 diabetes mellitus in Singapore children. Lee Y S, Ng W Y, Thai A C, Lui K F, Loke K Y. J Pediatr Endocrinol Metab. 2001 June; 14(6):767-72; A comparison of serum and EDTA plasma in the measurement of glutamic acid decarboxylase autoantibodies (GADA) and autoantibodies to islet antigen-2 (IA-2A) using the RSR radioimmunoassay (RIA) and enzyme linked immunosorbent assay (ELISA) kits. Rahmati K, Lernmark A, Becker C, Foltyn-Zadura A, Larsson K, Ivarsson S A, TC. Clin Lab. 2008; 54(7-8):227-35; GAD treatment and insulin secretion in recent-onset type 1 diabetes. Ludvigsson J, Faresj M, Hjorth M, Axelsson S, ChM, Pihl M, Vaarala O, Forsander G, Ivarsson S, Johansson C, Lindh A, Nilsson N O, Aman J, Ortqvist E, Zerhouni P, Casas R. N Engl J. Med. 2008 Oct. 30; 359(18):1909-20; Analysis of pancreas tissue in a child positive for islet cell antibodies. 23: Oikarinen M, Tauriainen S, Honkanen T, Vuori K, Karhunen P, Vasama-Nolvi C, Oikarinen S, Verbeke C, Blair G E, Rantala I, Ilonen J, Simell O, Knip M, HyH. Diabetologia. 2008 October; 51(10):1796-802; Autoimmune mechanisms in type 1 diabetes. Knip M, Siljander H. Autoimmun Rev. 2008 July; 7(7):550-7; A common nonsynonymous single nucleotide polymorphism in the SLC30A8 gene determines ZnT8 autoantibody specificity in type 1 diabetes. Wenzlau J M, Liu Y, Yu L, Moua O, Fowler K T, Rangasamy S, Walters J, Eisenbarth G S, Davidson H W, Hutton J C. Diabetes. 2008 October; 57(10):2693-7; Diabetes Antibody Standardization Program: evaluation of assays for autoantibodies to glutamic acid decarboxylase and islet antigen-2. Diabetes Antibody Standardization Program: evaluation of assays for autoantibodies to glutamic acid decarboxylase and islet antigen-2. Diabetologia. 2008 May; 51(5):846-52.

In one example of the present invention, in order to determine the expression profile of aminoacyl tRNA synthetases in a human pancreas, the inventors found positions of ARS, GRS, NRS and WRS in the pancreas by using indirect immunofluorescence by using an anti-ARS antibody, an anti-GRS antibody, an anti-NRS antibody, and an anti-WRS antibody. As a result, in can be found that ARS and GRS are mainly positioned in beta cells of langerhans islets (C and D in FIG. 1), and pancreatic ductal epithelial cells (areas indicated by arrows in C and D of FIG. 1). On the other hand, it can be found that NRS and WRS are uniformly distributed in langerhans islets and acinar cells within the pancreas (see E and F FIG. 1).

In another example of the present invention, from plasmas of type 1 and 2 diabetes mellitus patients, autoantibodies against aminoacyl tRNA synthetases were detected, and then it was determined if they can be utilized in diagnosis of type 1 diabetes mellitus. As a result, all of an anti-ARS antibody, an anti-GRS antibody, an anti-NRS antibody and an anti-WRS antibody were detected in a large amount in type 1 diabetes mellitus patients, compared to normal people and Type 2 diabetes mellitus patients, and thus it can be found that they can be used as a diagnostic marker for type 1 diabetes mellitus.

Advantageous Effects

Accordingly, the present invention provides, as a novel diagnosis marker for type 1 diabetes mellitus, a type diabetes mellitus diagnostic composition comprising alanyl-tRNA synthetase, glycyl-tRNA synthetase, asparaginyl-tRNA synthetase, or tryptophanyl-tRNA synthetase, a diagnostic kit comprising the same, and a diagnostic method using the same. The composition, the kit, and the method, according to the present invention, may be used for early diagnosis and confirmed diagnosis of type 1 diabetes mellitus because type 1 diabetes mellitus can be easily diagnosed from a patient sample.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR INVENTION

Figure 1:
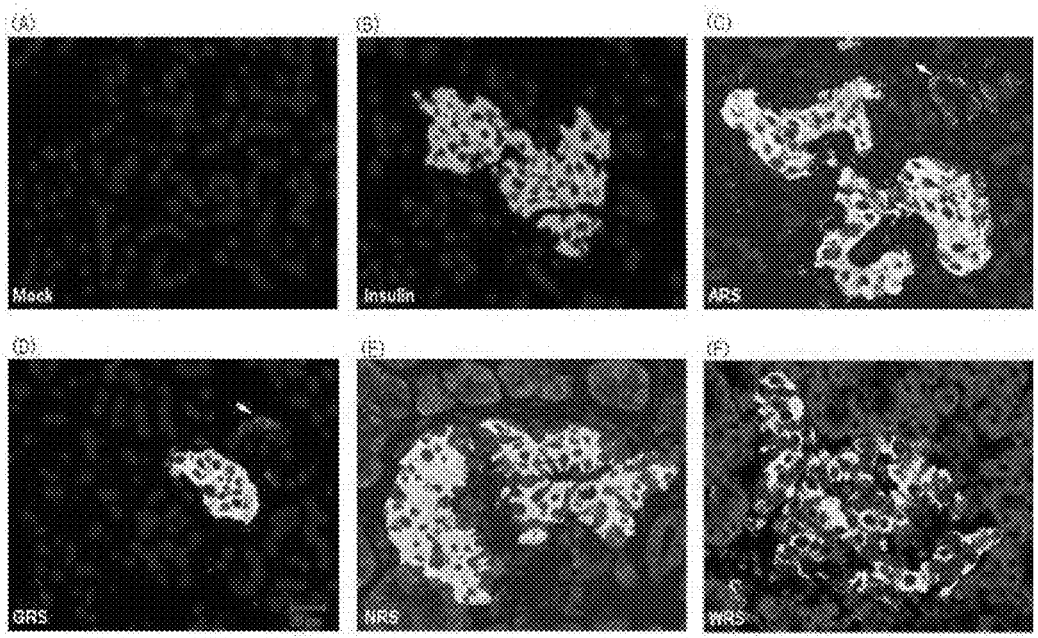
FIG. 1 is a result of immunofluorescence on ARS, GRS, NRS and WRS in the pancreas (A: Mock, B: insulin, C: ARS, D: GRS, E: NRS, F: WRS).

Hereinafter, the present invention will be described in detail with reference to Examples.

However, Examples below are intended to only illustrate the present invention, and are not intended to limit the scope of the present invention.

Example Method

1. Expression and Purification of Protein 1-685(GRS), 1-548(NRS), 1-968(AlaRS) and 1-471 (WRS) were PCR-amplified so that sequences to be encoded can be amplified. Each of a PCR product and a pET28a vector was treated with EcoRI/SalI, and then, cut and subcloned by pET28a (Novagen). The resultant product was added with 0.5 mM IPTG and subjected to overexpression in E. Coli BL21 for 12 hours at 23° C. (herein, inserted sequences of GRS, NRS, ARS, and WRS are denoted by sequence Nos. 5, 6, 7, and 8 respectively). The cell was collected and then dissolved through high frequency decomposition in buffer A (50 mM Tris-HCl, 50 mM NaCl, 0.5 mM EDTA, 2 mM 2-mercaptoethanol, pH 7.8), and was centrifuged at a rate of 22,000×g. After the centrifugation, the supernatant was subjected to precipitation through addition of ammonium sulfate while being slowly stirred. About 25 to 50% of the resultant product was dialyzed with buffer B (50 mM Tris-HCl, 100 mM NaCl, 0.5 mM EDTA, 2 mM 2-mercaptoethanol, 15% glycerol, pH 7.6), and then loaded on SP-sepharose column (BioRad). The resultant precipitated protein was eluted with 0.7 M NaCl concentration gradient and heparin column. The protein was loaded again on Ni++-column (Invitrogen), and eluted with 250 mM imidazole. The protein was dialyzed against 1×PBS and stored at 70° C.

2. ELISA

In order to detect autoantibodies of GAD and ICA, ELISA kits for GAD and ICA were bought from Biomerica, and ELISA was carried out under the manufacturer protocol. In order to analyze an aaRS autoantibody, each well was coated with 2 ng/Ml of ARSs at 4° C., for 12 hours, and blocked with PBS containing 2.5% BSA at room temperature for 1 hour. Then, 1/100 diluted serum was added to each well and cultured at room temperature for 1 hour. PBS containing 0.1% Tween 20 was used to wash the plate, and 1/10,000 diluted HRP-binding anti-human antibody was added to each well, followed by culturing at room temperature for 1 hour. The plate was washed with a washing buffer, and TMB (tetramethylbenzidine, Sigma) was added thereto, followed by a reaction for 20 minutes at a room temperature in a light-blocked state. Then, 1N HCl was added to stop the reaction, and then absorbance was measured at 405 nm.

3. Western Blot Using a Patient's Serum

Each purified aaRSs 10 ng was loaded on 10% SDS-PAGE, and transferred onto PVDF membrane (0.4 μm, Millipore).

The membrane was blocked with TBST (20 mM Tris-HCl, 130 mM NaCl, 0.2% Tween 20) containing 5% BSA at room temperature for 1 hour. Meanwhile, the inventors of the present invention diluted each patient sample up to 1/100 by using TBST containing 1% BSA, and cultured the membrane at room temperature for 1 hour. They washed the membrane, and added 1/10,000 diluted HRP (horseradish peroxidase) binding anti-human antibody to the membrane, followed by a reaction.

Example Result

1. Immunofluorescence of aaRSs (Aminoacyl-tRNA Synthetases) in the Pancreas

From recently conducted researches, it was determined that expression of some aaRSs frequently occurred in the pancreas. In order to determine the expression profile of aaRSs in a human pancreas, the inventors of the present invention generated a specific antibody of each aaRS, and found positions of ARS, -GRS, -NRS and -WRS in the pancreas by using indirect immunofluorescence.

As a result, in can be found that ARS and GRS are mainly specifically positioned in beta cells of langerhans islets (C and D in FIG. 1), and pancreatic ductal epithelial cells (areas indicated by arrows in C and D of FIG. 1). On the other hand, it can be found that NRS and WRS are uniformly distributed in langerhans islets and acinar cells within pancreas (see E and F FIG. 1).

2. Analysis of Autoantibody by Using Human Plasma

An autoantibody against aaRSs is discovered from an autoimmune disease patient, and type 1 diabetes mellitus (type 1 DM) is caused by autoimmunity through destruction of β-cells in the pancreas. Accordingly, the inventors of the present invention determined if diabetes mellitus can be diagnosed based on the existence of an anti-aaRSs autoantibody in plasmas of a normal person, and type 1 and 2 diabetes mellitus patients, and if the autoantibody can be a diagnostic marker for diabetes mellitus.

They coated respective wells in 96 well-plate, with respective purified aaRSs, and loaded plasmas of normal people (n=65), type 1 diabetes mellitus patients (n=58), and Type 2 diabetes mellitus patients (n=60) so as to detect an anti-aaRS autoantibody.

Figure 2:
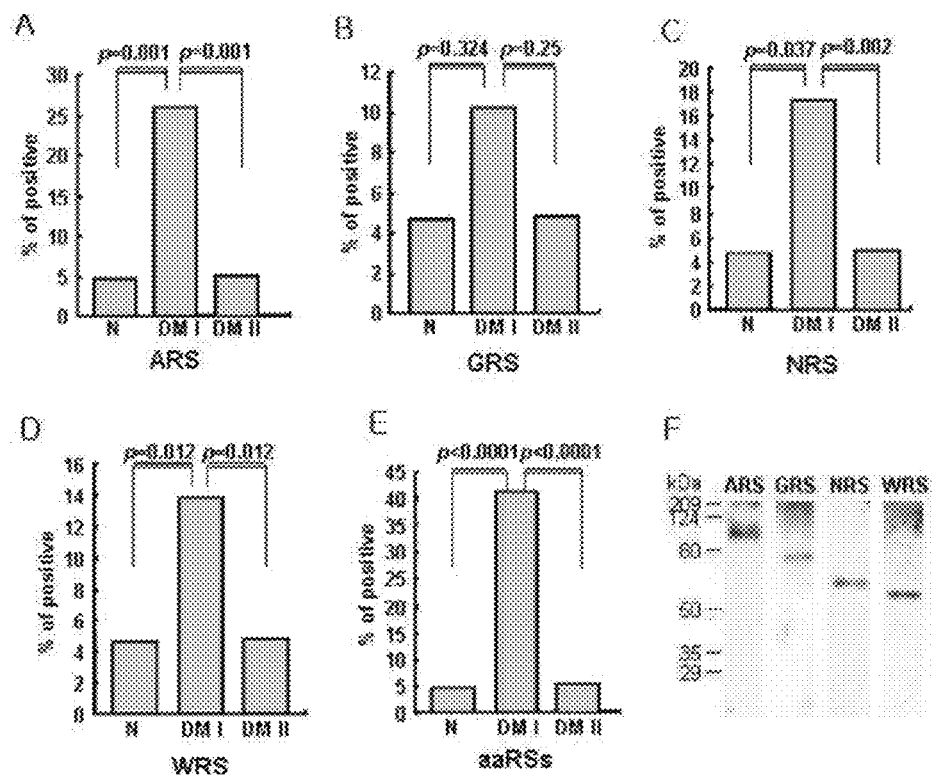
FIG. 2 is a result of detection of an autoantibody against each aminoacyl tRNA synthetase in plasma (A: ARS, B: GRS, C: NRS, D: WRS, E: aminoacyl tRNA synthetase, F: immunoblot result through ARS, GRS, NRS and WRS in plasma).

As a result, an anti-ARS autoantibody was discovered in a ratio of 4.6% of normal people, in a ratio of 25.9% of type 1 diabetes mellitus patients, and in a ratio of 5% of Type 2 diabetes mellitus patients (see FIG. 2A). An anti-GRS autoantibody was discovered in a ratio of 4.6% of normal people, in a ratio of 10.3% of type 1 diabetes mellitus patients, and in a ratio of 5% of Type 2 diabetes mellitus patients (see FIG. 2B). An anti-NRS autoantibody was discovered in a ratio of 4.6% of normal people, in a ratio of 17.2% of type 1 diabetes mellitus patients, and in a ratio of 5% of Type 2 diabetes mellitus patients (see FIG. 2C). An anti-WRS autoantibody was discovered in a ratio of 4.6% of normal people, in a ratio of 13.8% of type 1 diabetes mellitus patients, and in a ratio of 5% of Type diabetes mellitus patients (see FIG. 2D). Through the results, it can be found that 41.3% of plasmas of type 1 diabetes mellitus patients have the anti-aaRS antibody while only 5% of plasmas of normal people and Type 2 diabetes mellitus patients have the anti-aaRS antibody.

Next, the inventors determined if an anti-aaRS antibody-positive plasma can specifically recognize each aaRS. They carried out immunoblot by ARS, GRS, NRS and WRS, and as a result, found that a human plasma can specifically recognize each aaRS.

Through the result, it can be found that an anti-aaRS antibody is specifically discovered in type 1 diabetes mellitus, and can be a diagnostic marker for type 1 diabetes mellitus.

3. Analysis of Difference Between aaRSs by GAD and ICA

Figure 3:
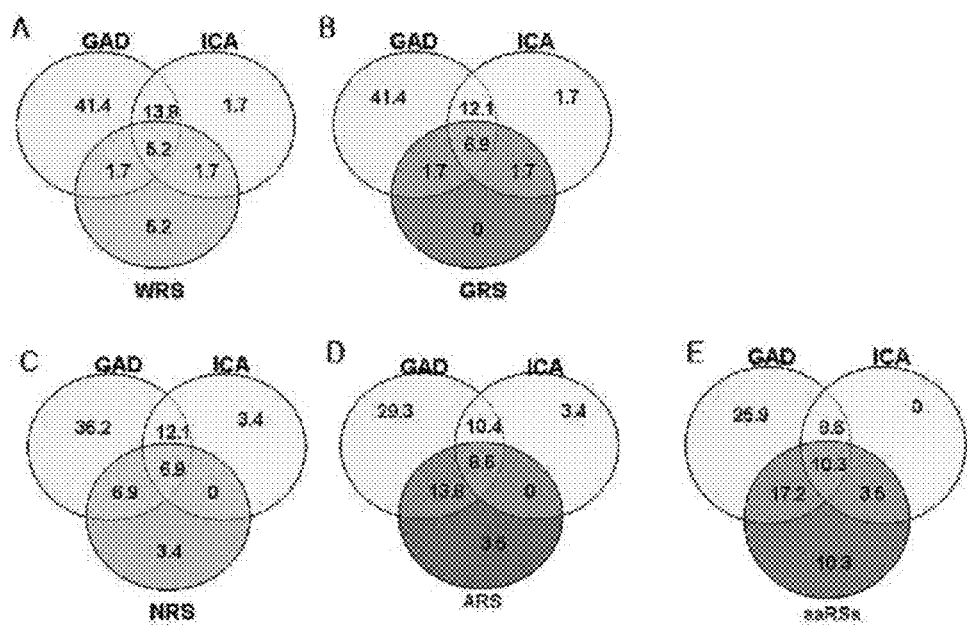
FIG. 3 shows classifications of autoantibodies specific to GAD, ICA and aaRS (A: WRS, B: GRS, C: NRS, D: ARS, E: aminoacyl tRNA synthetase).

In order to analyze the difference between aaRSs in an autoantibody through GAD and ICA, the inventors carried out ELISA by using a detection kit for anti-GAD and anti-ICA. In analysis using type 1 diabetes mellitus plasma, an anti-GAD antibody and an anti-ICA antibody were discovered in ratios of 62.1% and 22.4%, respectively. Then, 19% of patients were double positive (see FIG. 3A).

Then, the inventors analyzed by antibodies against GAD and ICA, if each aaRS antibody can distinguishably diagnose type 1 diabetes mellitus. For an anti-WRS antibody, an overlapping ratio in both anti-GAD antibody and anti-ICA antibody was 5.2%, and an overlapping ratio in anti-GAD antibody or anti-ICA antibody was 1.7%. Thus, they found that 5.2% with respect to 13.2% was specific to WRS. For an anti-GRS antibody, an overlapping ratio in both anti-GAD antibody and anti-ICA antibody was 6.9%, and an overlapping ratio in anti-GAD antibody or anti-ICA antibody was 1.7%. Thus, they found that there is no autoantibody only specific to GRS. For an anti-NRS antibody, an overlapping ratio in both anti-GAD antibody and anti-ICA antibody was 6.9%, and an overlapping ratio in anti-GAD antibody was 6.9%. Thus, they found that 3.4% with respect to 17.2% was specific to NRS. For an anti-ARS antibody, an overlapping ratio in both anti-GAD antibody and anti-ICA antibody was 8.6%, and an overlapping ratio in anti-GAD antibody was 13.8%. Thus, they found that 3.5% with respect to 25.9% was specific to ARS. When all anti-aaRS antibodies were used in an analysis, an overlapping ratio in both anti-GAD antibody and anti-ICA antibody was 10.3%, and overlapping ratios in anti-GAD antibody and anti-ICA antibody, respectively, were 17.2% and 3.5%.

Through the test results, it can be found that 10.3% with respect to 41.35% was specific as anti-aaRS, and especially, there is no specific ICA.

INDUSTRIAL APPLICABILITY

As can be seen foregoing, the present invention provides, as a novel diagnosis marker for type 1 diabetes mellitus, a type 1 diabetes mellitus diagnostic composition comprising alanyl-tRNA synthetase, glycyl-tRNA synthetase, asparaginyl-tRNA synthetase, or tryptophanyl-tRNA synthetase, a diagnostic kit comprising the same, and a diagnostic method using the same. The composition, the kit, and the method, according to the present invention, may be used for early diagnosis and confirmed diagnosis of type 1 diabetes mellitus because type 1 diabetes mellitus can be easily diagnosed from a patient sample.

The invention claimed is:

1. A method for diagnosing type 1 diabetes mellitus comprising:

obtaining a sample from a subject suspected of having type 1 diabetes mellitus;

contacting the sample with two or more purified recombinant proteins selected from the group consisting of alanyl tRNA synthetase, glycyl tRNA synthetase, asparaginyl tRNA synthetase, and tryptophanyl tRNA synthetase, and fragments thereof;

detecting the binding of two or more of an anti-alanyl tRNA synthetase antibody, an anti-glycyl tRNA synthetase antibody, an anti-asparaginyl tRNA synthetase antibody, and an anti-tryptophanyl tRNA synthetase antibody in the sample with the two or more purified recombinant proteins, wherein detecting the binding of two or more of the antibodies with the two or more purified recombinant proteins indicates that the subject has type 1 diabetes mellitus.

2. The method of claim 1, further comprising a step of:

detecting a marker for diagnosis of type 1 diabetes mellitus selected from the group consisting of anti-Glutamate decarboxylase 65 (GAD65) antibody, anti-islet antigen-2 (IA-2) antibody, anti-insulin antibody, anti-islet-cell antigen (ICA) antibody, hemoglobin A1C (HbA1C) level, C-peptide level, and Solute Carrier Family 30-Member 8 (Slc30A8) level in the sample obtained from the subject.

3. A method for diagnosing type 1 diabetes mellitus consisting of:

obtaining a sample from a subject suspected of having type 1 diabetes mellitus;

contacting the sample with two or more purified recombinant proteins selected from the group consisting of alanyl tRNA synthetase, glycyl tRNA synthetase, asparaginyl tRNA synthetase, and tryptophanyl tRNA synthetase, and fragments thereof;

detecting the binding of two or more of an anti-alanyl tRNA synthetase antibody, an anti-glycyl tRNA synthetase antibody, an anti-asparaginyl tRNA synthetase antibody, and an ant-tryptophanyl tRNA synthetase antibody in the sample with the two or more purified recombinant proteins, wherein detecting the binding of two or more of the antibodies with the two or more purified recombinant proteins indicates that the subject has type 1 diabetes mellitus.

4. A method for diagnosing type 1 diabetes mellitus consisting of:

obtaining a sample from a subject suspected of having type 1 diabetes mellitus;

contacting the sample with two or more purified recombinant proteins selected from the group consisting of alanyl tRNA synthetase, glycyl tRNA synthetase, asparaginyl tRNA synthetase, and tryptophanyl tRNA synthetase, and fragments thereof;

detecting the binding of two or more of an anti-alanyl tRNA synthetase antibody, an anti-glycyl tRNA synthetase antibody, an anti-asparaginyl tRNA synthetase antibody, and an anti-tryptophanyl tRNA synthetase antibody in the sample with the two or more purified recombinant proteins;

detecting a marker for diagnosis of type 1 diabetes mellitus selected from the group consisting of anti-Glutamate decarboxylase 65 (GAD65) antibody, anti-islet antigen-2 (IA-2) antibody, anti-insulin antibody, anti-islet-cell antigen (ICA) antibody, hemoglobin A1C (HbA1C) level, C-peptide level, and Solute Carrier Family 30-Member 8 (Slc30A8) level in the sample;

wherein detecting the binding of two or more of the antibodies with the two or more purified recombinant proteins and the presence of the marker for diagnosis of type 1 diabetes mellitus in the sample indicates that the subject has type 1 diabetes mellitus.

* * * * *